(12) United States Patent
McEntire et al.

(10) Patent No.: US 12,017,912 B2
(45) Date of Patent: *Jun. 25, 2024

(54) ANTIPATHOGENIC DEVICES AND METHODS THEREOF

(71) Applicant: SINTX Technologies, Inc., Salt Lake City, UT (US)

(72) Inventors: Bryan J. McEntire, Salt Lake City, UT (US); Ryan M. Bock, Salt Lake City, UT (US); Bhajanjit Singh Bal, Salt Lake City, UT (US)

(73) Assignee: SINTX Technologies, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/062,681

(22) Filed: Dec. 7, 2022

(65) Prior Publication Data

US 2023/0099133 A1    Mar. 30, 2023

Related U.S. Application Data

(60) Continuation of application No. 17/521,270, filed on Nov. 8, 2021, now Pat. No. 11,591,217, which is a division of application No. 16/550,605, filed on Aug. 26, 2019, now Pat. No. 11,192,787.

(60) Provisional application No. 62/800,034, filed on Feb. 1, 2019, provisional application No. 62/727,724, filed on Sep. 6, 2018.

(51) Int. Cl.
| | |
|---|---|
| *C01B 21/068* | (2006.01) |
| *A01C 1/06* | (2006.01) |
| *A01N 25/32* | (2006.01) |
| *A01N 59/02* | (2006.01) |

(52) U.S. Cl.
CPC ............ *C01B 21/068* (2013.01); *A01C 1/06* (2013.01); *A01N 25/32* (2013.01); *A01N 59/02* (2013.01)

(58) Field of Classification Search
None
See application file for complete search history.

(56) References Cited

U.S. PATENT DOCUMENTS

| | | | |
|---|---|---|---|
| 6,302,913 B1 | 10/2001 | Ripamonti et al. | |
| 7,776,085 B2 | 8/2010 | Bemero et al. | |
| 9,925,295 B2 | 3/2018 | McEntire et al. | |
| 10,806,831 B2 | 10/2020 | McEntire et al. | |
| 11,192,787 B2 * | 12/2021 | McEntire | C01B 21/068 |
| 2004/0000313 A1 | 1/2004 | Gaynor et al. | |
| 2005/0079379 A1 | 4/2005 | Wadsworth et al. | |
| 2005/0182152 A1 | 8/2005 | Nonninger et al. | |
| 2006/0052875 A1 | 3/2006 | Bernero et al. | |
| 2009/0041818 A1 | 2/2009 | Otsuki et al. | |
| 2009/0320172 A1 | 12/2009 | Slate et al. | |
| 2010/0040655 A1 | 2/2010 | Ren et al. | |
| 2010/0136325 A1 | 6/2010 | Reddy et al. | |
| 2012/0060258 A1 | 3/2012 | Stewart et al. | |
| 2013/0236854 A1 | 9/2013 | McEntire et al. | |
| 2013/0302509 A1 | 11/2013 | McEntire et al. | |
| 2013/0302512 A1 | 11/2013 | McEntire et al. | |
| 2016/0339144 A1 | 11/2016 | McEntire et al. | |
| 2017/0197014 A1 | 7/2017 | McEntire et al. | |
| 2020/0079651 A1 | 3/2020 | McEntire et al. | |
| 2022/0055899 A1 | 2/2022 | McEntire et al. | |
| 2022/0315941 A1 * | 10/2022 | Flavell | C12N 15/8293 |

FOREIGN PATENT DOCUMENTS

| | | |
|---|---|---|
| CN | 101453995 A | 6/2009 |
| CN | 102805081 A | 12/2012 |
| CN | 107926975 A | 4/2018 |
| CN | 112911944 A | 6/2021 |
| EP | 0807766 B1 | 12/2003 |
| JP | 2009526828 A | 7/2009 |
| JP | 2015516239 A | 6/2015 |
| JP | 2020019677 A | 2/2020 |
| KR | 1020090003230 A | 1/2009 |
| KR | 1020150005986 A | 1/2015 |
| WO | 2011067005 A1 | 6/2011 |
| WO | 2020051004 A1 | 3/2020 |

OTHER PUBLICATIONS

US 6,117,172 A, 09/2000, Ripamonti et al. (withdrawn)
IP Australia, Examination Report No. 2 for Standard Patent Application, Application No. 2019336133, dated May 3, 2023, 5 pages.
China National Intellectual Property Administration (CNIPA), First Office Action, Application No. 201980058291.0, Mar. 8, 2023, 18 pages.
Japan Patent Office, Notice of Reasons for Rejection, Application No. 2021-510805, mailing date Jan. 24, 2023, 5 pages.
IP Australia, Examination Report No. 1 for Standard Patent Application, Application No. 2019336133, date Jan. 20, 2023, 4 pages.
Indian Patent Office, First Examination Report issued in corresponding Indian Application No. 202137015785, Feb. 21, 2022, 7 pages.
European Patent Office, Extended European Search Report issued in corresponding Application No. 19856613.5, May 2, 2022, 10 pages.
Canadian Intellectual Property Office, Office Action, Application No. 3,109,874, dated Nov. 25, 2022, 4 pages.
U.S. Patent and Trademark Office, Final Office Action, U.S. Appl. No. 17/230,284, dated Apr. 6, 2023, 9 pages.
U.S. Patent and Trademark Office, Final Office Action, U.S. Appl. No. 17/230,402, dated Apr. 14, 2023, 11 pages.
U.S. Patent and Trademark Office, Office Action issued in related Application No. 17/230,395 on Oct. 28, 2022, 11 pages.

(Continued)

*Primary Examiner* — Alton N Pryor
(74) *Attorney, Agent, or Firm* — Polsinelli PC

(57) ABSTRACT

Disclosed herein are compositions, devices and methods for inactivating viruses, bacteria, and fungi. The compositions, methods, and devices may include coatings or slurries such as silicon nitride powder coatings or slurries for the inactivation of viruses, bacteria, and/or fungi.

13 Claims, 19 Drawing Sheets

(56) References Cited

OTHER PUBLICATIONS

U.S. Patent and Trademark Office, Office Action issued in related Application No. 17/230,284 on Oct. 28, 2022, 10 pages.
Pezzetti et al., Rapid Inactivation of SARS-CoV-2 by Silicon Nitride, Copper, and Aluminum Nitride, 2020, 16 pages.
Lehman et al., "Silicon nitride inactivates SARS-CoV-2 in vitro, bioRxiv," 2020, 1-11. (Year: 2020).
Pezzotti et al., "Instantaneous catch-and-kill inactivation of SARS-CoV-2 by nitride ceramics," Clinical and Translational Medicine (2020), 10(6), e212 ). (Year: 2020)
U.S. Patent and Trademark Office, Non-Final Office Action, U.S. Appl. No. 17/230,395, dated Apr. 6, 2023, 11 pages.
U.S. Patent and Trademark Office, Final Office Action, U.S. Appl. No. 17/230,402, dated Oct. 28, 2022, 11 pages.
China National Intellectual Property Administration, Second Office Action, Application No. 201980058291.0, 22 pages.
Korean Intellectual Property Office, Notification of Provisional Rejection, Application No. 10-2021-7009890, Jan. 12, 2024, 17 pages.
Japan Patent Office, Decision of Refusal, Application No. 2021-510805, Jul. 18, 2023, 3 pages.
Brazilian Patent Office (INPI), Preliminary Office Action, Application No. BR112021002911-7, Aug. 1, 2023 , 5 pages.
European Patent Office, Partial Supplementary European Search Report, Application No. 21788806.4, Mar. 27, 2024, 12 pages.

* cited by examiner

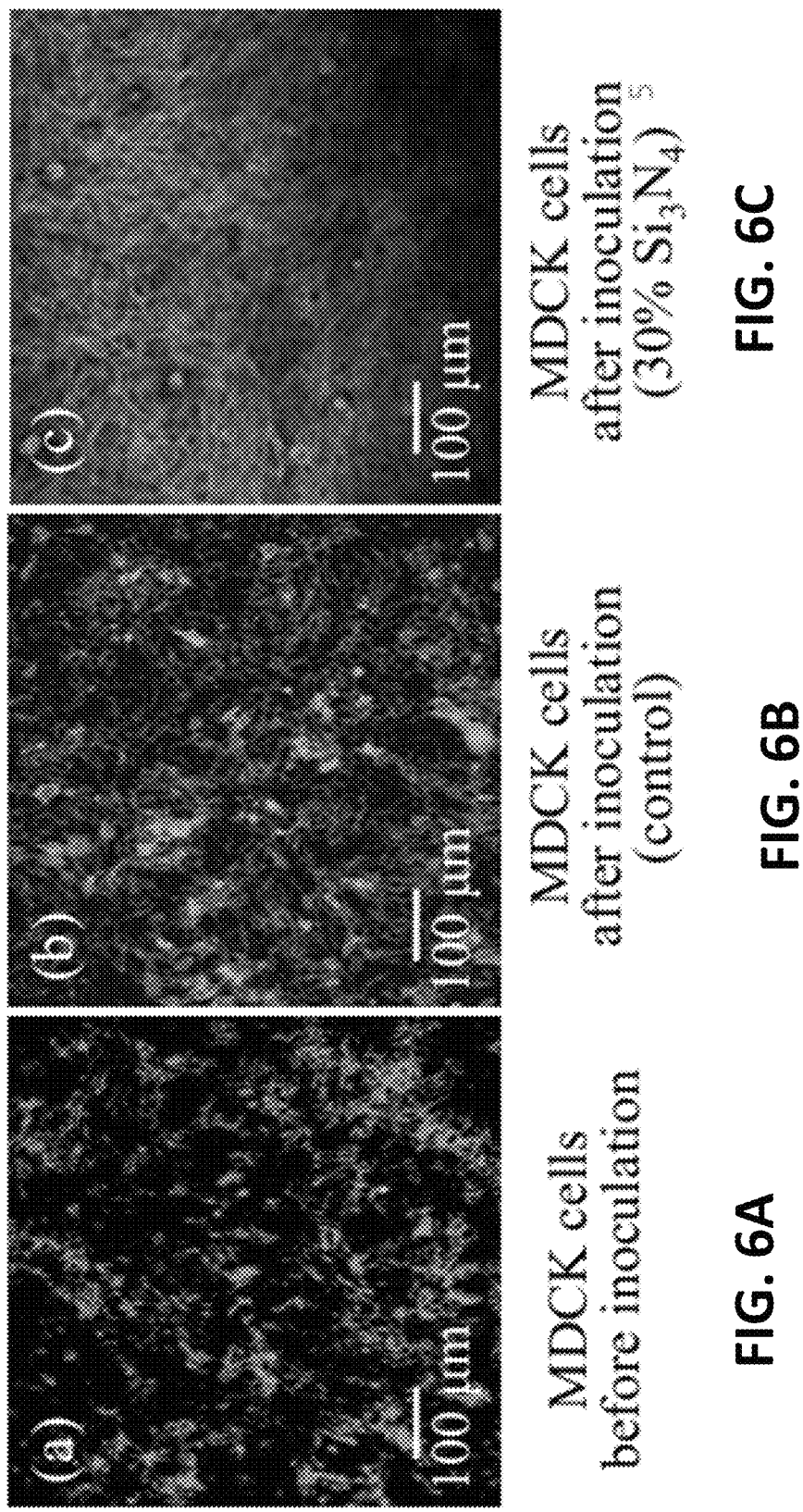

FIG. 10

NP + F-actin

Viral NP

F-actin

NP + F-actin

Viral NP

F-actin

*Untreated spore sacs*

*Spore sacs in presence of $Si_3N_4$*

ANTIPATHOGENIC DEVICES AND METHODS THEREOF

CROSS REFERENCE TO RELATED APPLICATIONS

This application is a continuation application of Ser. No. 17/521,270, filed Nov. 8, 2021, which is a divisional application of Ser. No. 16/550,605, filed Aug. 26, 2019 now U.S. Pat. No. 11,192,787, which claims the benefit of U.S. Provisional Application No. 62/727,724, filed Sep. 6, 2018, and U.S. Provisional Application No. 62/800,034, filed Feb. 1, 2019, the contents of which are entirely incorporated by reference herein.

FIELD

The present disclosure relates to antiviral, antibacterial, and antifungal composition, systems, methods, and devices. More specifically, the disclosure relates to silicon nitride compositions, devices, and coatings for the inactivation and lysis of viruses, bacteria, and fungi.

BACKGROUND

The need for safe and reliable inactivation, removal, or lysis of viruses, bacteria, and fungi is universal. There is a broad need to control the pathogens that affect human health and agricultural products. Not only is there a need for materials that possess antipathogenic properties for human medicinal therapies, but also for use as surface coatings and/or composites for various medical devices or equipment, examination tables, clothing, filters, masks, gloves, catheters, endoscopic instruments, and the like.

Furthermore, application of antipathogenic materials is greatly needed in agriculture. Up to 15% of the world's edible annual crops are destroyed due to their susceptibility to plant-based viruses, bacteria, and fungi. For example, *Plasmopara viticola* is considered to be one of the most devastating diseases of grape vines in climates with relatively warm and humid summers and has markedly reduced crop yields in France, Spain, and Italy. Furthermore, there is increasing concern that the mycotoxins produced by these fungi have an overall negative impact on human health and longevity. Conventional pharmaceutical pathogen inactivation methods include the use of specially engineered organic petrochemicals, antibiotics, genetic engineering, or through the use of solid-state inactivators (e.g., cuprous oxide, $Cu_2O$, and silver nitrate, $AgNO_3$). While these therapies are quite effective, there are significant environmental health and safety concerns with their use. New petrochemical compounds may have chronic residual effects to humans, wildlife, plants, and soil. Extensive use of antibiotics in humans, animals and on agricultural crops increases the inherent resistance of bacterial pathogens. Genetic engineering of crops to resist disease is increasingly unpopular and politically unpalatable. Solid-state inactivators release Cu and Ag ions which might induce damage to mammalian cells. In addition, each of these approaches to the control of pathogens has come under increased regulatory scrutiny.

Therefore, there is a need for safe and reliable methods to inactivate and kill viruses, bacteria, and fungi that may be applied to medical devices, equipment, clothing, or other systems which may have prolonged contact with the human body or be used in various agricultural applications to treat viral or bacterial diseases and fungal infections.

SUMMARY

Provided herein is a device having silicon nitride on at least a portion of a surface of the device, wherein the silicon nitride is present in a concentration sufficient to inactivate a pathogen on the surface of the device. The device may include a silicon nitride coating. The silicon nitride may present in a concentration of about 1 wt. % to about 100 wt. %, for example 15 wt. % silicon nitride. Also provided herein is a method of treating or preventing a pathogen at a location in a human patient. The method may include contacting the patient with a device comprising silicon nitride. In another aspect, a method of inactivating a pathogen may include contacting an apparatus comprising silicon nitride at a concentration of about 1 wt. % to about 100 wt. % with the virus. The methods may further include coating the apparatus with a silicon nitride powder on the surface of the apparatus and/or incorporating a silicon nitride powder within the apparatus. The silicon nitride in the device, apparatus, and/or coating may be present in a concentration sufficient to inactivate the pathogen. The apparatus may be in contact with a patient for as long as needed to inactivate the pathogen. For example, the apparatus may be in contact with the patient for at least 1 minute or may be permanently implanted within the patient.

The silicon nitride in the device or apparatus may be present in the form of a powder. In an aspect, the pathogen may be Influenza A. The silicon nitride may decrease viral action by alkaline transesterification and reduce the activity of hemagglutinin.

Further provided herein is a composition for inactivating a pathogen may include silicon nitride in a concentration of about 1 vol. % to about 30 vol. %, for example about 1.5 vol % silicon nitride. In another aspect, a method of inactivating a pathogen may include contacting a composition comprising silicon nitride at a concentration of about 1 vol. % to about 30 vol. % with the pathogen. The method may further include spraying the composition onto the surface of a plant to contact the pathogen. The composition may be in contact with the pathogen for at least 1 minute. The composition may include a slurry of silicon nitride particles and water.

The silicon nitride may be present in a concentration sufficient to inactivate the pathogen. The silicon nitride particles may attach to spores of the pathogen. The pathogen may be *Plasmopara viticola*. The plant may be Cabernet Sauvignon or Cannonau.

Further provided herein is a method of treating or preventing a pathogen at a location in on a plant. The method may include contacting the plant with a slurry comprising silicon nitride. The slurry may include about 1 vol. % to about 30 vol. % silicon nitride. The silicon nitride may be present in the in a concentration sufficient to inactivate the pathogen. In some aspects, the pathogen is *Plasmopara viticola*, and the plant is Cabernet Sauvignon or Cannonau. The composition may be in contact with the pathogen for at least 1 minute.

Other aspects and iterations of the invention are described more thoroughly below.

BRIEF DESCRIPTION OF THE DRAWINGS

FIG. 6A shows a fluorescence microscopy image of MDCK cells before inoculation.

FIG. 6B shows a fluorescence microscopy image of MDCK cells after inoculation with a virus exposed to the control.

FIG. 6C shows a fluorescence microscopy image of MDCK cells after inoculation with a virus exposed to 30 wt. % $Si_3N_4$.

Figure 10:
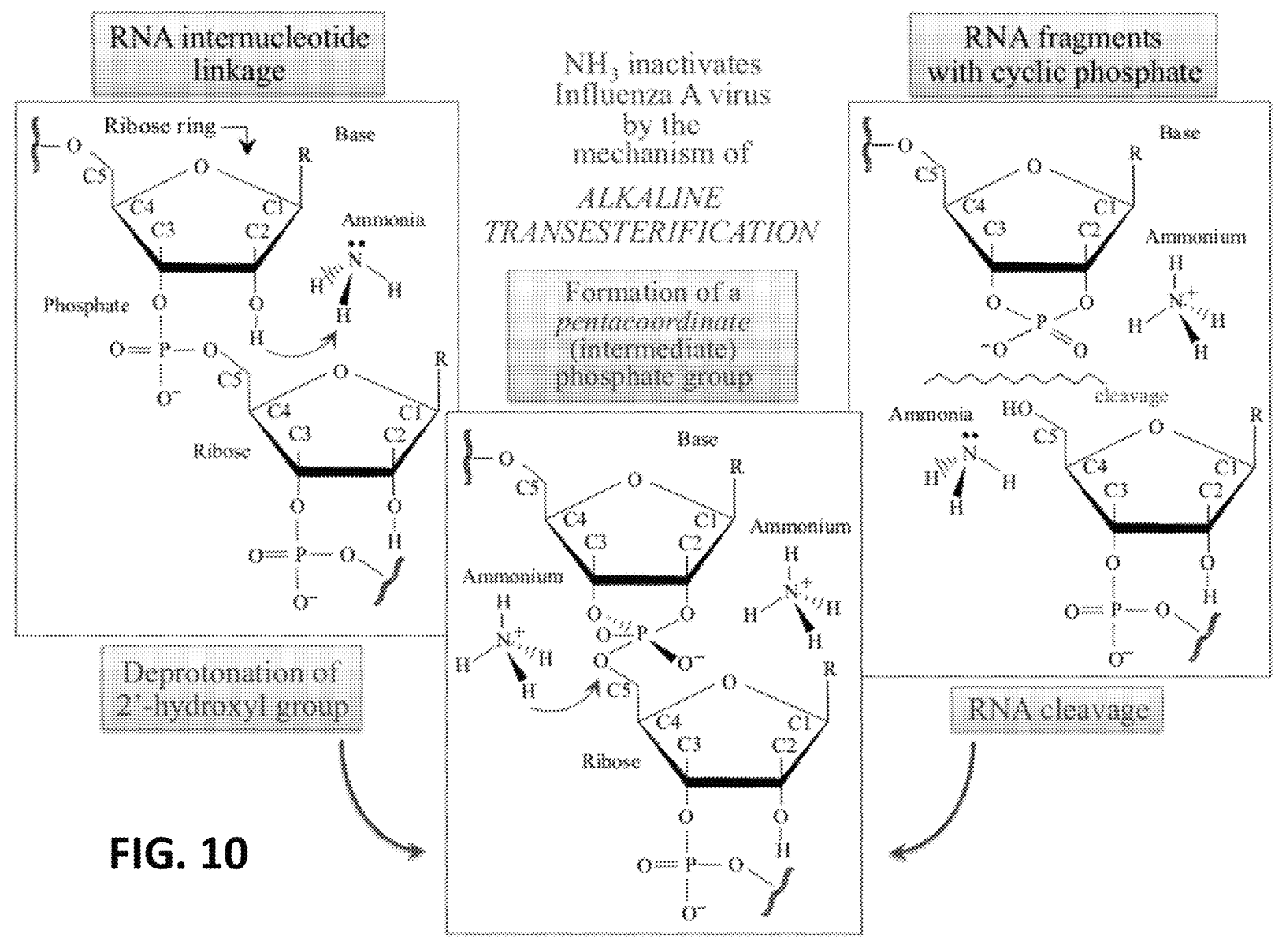

FIG. 10 shows $NH_3$ inactivates Influenza A virus by the mechanism of alkaline transesterification.

DETAILED DESCRIPTION

Figure 1:
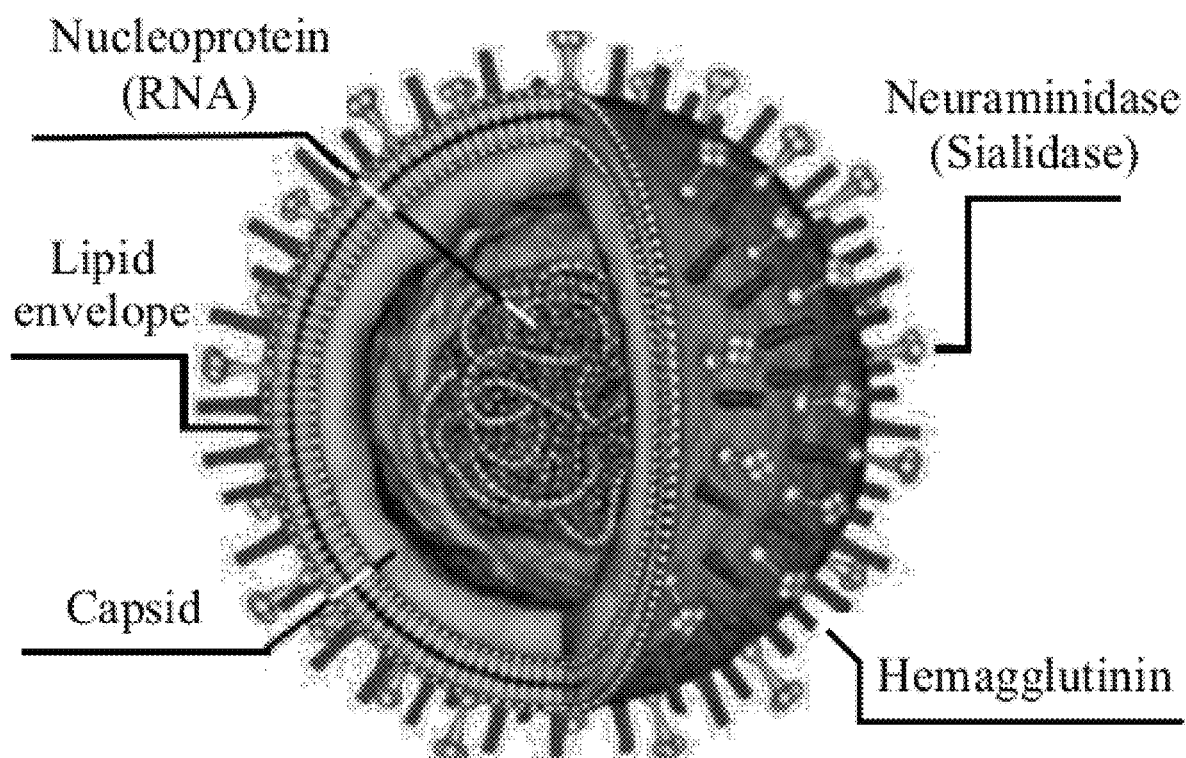
FIG. 1 is an illustration of the Influenza A virus.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure. Thus, the following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be references to the same embodiment or any embodiment; and, such references mean at least one of the embodiments.

Reference to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others.

The term "apparatus" as used herein includes compositions, devices, surface coatings, and/or composites. In some examples the apparatus may include various medical devices or equipment, examination tables, clothing, filters, masks, gloves, catheters, endoscopic instruments, and the like. The apparatus may be metallic, polymeric, and/or ceramic (ex. silicon nitride and/or other ceramic materials).

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any example term. Likewise, the disclosure is not limited to various embodiments given in this specification.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

Provided herein are antipathogenic devices, compositions, and apparatuses that include silicon nitride ($Si_3N_4$) for the inactivation of viruses, bacteria, and fungi. Silicon nitride possesses a unique surface chemistry which is biocompatible and provides a number of biomedical applications including 1) concurrent osteogenesis, osteoinduction, osteoconduction, and bacteriostasis, such as in spinal and dental implants; 2) killing of both gram-positive and gram-negative bacteria according to different mechanisms; 3) inactivation of human and animal viruses, bacteria, and fungi as well as plant-based viruses, bacteria, and fungi; and 4) polymer- or metal-matrix composites, natural or man-made fibers, polymers, or metals containing silicon nitride powder retain key silicon nitride bone restorative, bacteriostatic, antiviral, and antifungal properties.

In an embodiment, an antipathogenic composition may include silicon nitride. For example, the antipathogenic composition may include silicon nitride powder. In some embodiments, the antipathogenic composition may be a monolithic component comprising 100% silicon nitride. Such a component can be fully dense possessing no internal porosity, or it may be porous, having a porosity that ranges from about 1% to about 80%. The monolithic component may be used as a medical device or may be used in an apparatus in which the inactivation of a virus, bacteria, and/or fungi may be desired. In another embodiment, antipathogenic composition may be incorporated within a device or in a coating to inactivate viruses, bacteria, and fungi. In some embodiments, the antipathogenic composition may be a slurry comprising silicon nitride powder. For example, the antipathogenic composition may be sprayed onto the surface of plants for the inactivation of agricultural pathogens.

In some embodiments, the antipathogenic composition may inactivate human viruses, bacteria, and/or fungi. Non-limiting examples of viruses that may be inactivated by the antipathogenic composition include Influenza A and Feline calicivirus. For example, a silicon nitride bioceramic may be effective in the inactivation of the Influenza A virus. In some embodiments, a silicon nitride coating may decrease antibacterial and antiviral resistance and/or promote bone tissue restoration. In some embodiments, the antipathogenic composition may inactivate agricultural viruses, bacteria, and/or fungi. Non-limiting examples of agricultural fungi that may be inactivated by the antipathogenic composition include *Plasmopara viticola* (downy mildew) or similar plant pathogens.

Without being limited to a particular theory, silicon nitride may provide a surface chemistry such that ammonia ($NH_3$) is available for virus, bacteria, or fungi inactivation. The surface chemistry of silicon nitride may be shown as follows:

$$Si_3N_4 + 6H_2O \rightarrow 3SiO_2 + 4NH_3$$

$$SiO_2 + 2H_2O \rightarrow Si(OH)_4$$

Nitrogen elutes faster (within minutes) than silicon because surface silanols are relatively stable. For viruses, it was surprisingly found that silicon nitride may provide for RNA cleavage via alkaline transesterification which leads to loss in genome integrity and virus inactivation. This may also reduce the activity of hemagglutinin.

In an embodiment, the antipathogenic composition may exhibit elution kinetics that show: (i) a slow but continuous elution of ammonia from the solid state rather than from the usual gas state; (ii) no damage or negative effect to cells; and (iii) an intelligent elution increasing with decreasing pH. The inorganic nature of silicon nitride may be more beneficial than the use of petrochemical or organometallic fungicides which are known to have residual effects in soil, on plants, and in their fruit.

A device or apparatus may include silicon nitride on at least a portion of a surface of the device for antiviral, antibacterial, or antifungal action. In an embodiment, a device may include a silicon nitride coating on at least a portion of a surface of the device. The silicon nitride coating may be applied to the surface of the device as a powder. In some embodiments, the powder may be micrometric in size. In other embodiments, the silicon nitride may be incorporated into the device. For example, a device may incorporate silicon nitride powder within the body of the device. In one embodiment, the device may be made of silicon nitride.

The silicon nitride coating may be present on the surface of a device in a concentration of about 1 wt. % to about 100 wt. %. In various embodiments, the coating may include about 1 wt. %, 2 wt. %, 5 wt. %, 7.5 wt. %, 8.3 wt. %, 10 wt. %, 15 wt. %, 16.7 wt. %, 20 wt. %, 25 wt. %, 30 wt. %, 33.3 wt. %, 35 wt. %, or 40 wt. % silicon nitride powder. In at least one example, the coating includes about 15 wt. % silicon nitride. In some embodiments, silicon nitride may be present in or on the surface of a device or apparatus in a concentration of about 1 wt. % to about 100 wt. %. In various embodiments, a device or apparatus may include about 1 wt. %, 2 wt. %, 5 wt. %, 7.5 wt. %, 8.3 wt. %, 10 wt. %, 15 wt. %, 16.7 wt. %, 20 wt. %, 25 wt. %, 30 wt. %, 33.3 wt. %, 35 wt. %, 40 wt. %, 50 wt. %, 60 wt. %, 60 wt. %, 70 wt %, 80 wt. %, 90 wt. %, to 100 wt. % silicon nitride.

In various embodiments, a device or apparatus that includes silicon nitride for antipathogenic properties may be a medical device. Non-limiting examples of devices or apparatuses include orthopedic implants, spinal implants, pedicle screws, dental implants, in-dwelling catheters, endotracheal tubes, colonoscopy scopes, and other similar devices.

In some embodiments, silicon nitride may be incorporated within or applied as a coating to materials or apparatuses for antipathogenic properties such as polymers and fabrics, surgical gowns, tubing, clothing, air and water filters, masks, tables such as hospital exam and surgical tables, desks, toys, filters such as air conditioner filters, or toothbrushes.

In other embodiments, silicon nitride powder may be incorporated into compositions including, but not limited to slurries, suspensions, gels, sprays, or toothpaste. In other embodiments, silicon nitride may be mixed with water along with any appropriate dispersants and slurry stabilization agents, and thereafter applied by spraying the slurry onto various agricultural plants, fruit-trees, vines, grain crops, and the like. For example, a silicon nitride slurry may be sprayed on fungi infected grape leaves.

In an example, the antipathogenic composition may be a slurry of silicon nitride powder and water. The silicon nitride powder may be present in the slurry in a concentration of about 0.1 vol. % to about 20 vol. %. In various embodiments, the slurry may include about 0.1 vol. %, 0.5 vol. %, 1 vol. %, 1.5 vol. %, 2 vol. %, 5 vol. %, 10 vol. %, 15 vol. %, or 20 vol. % silicon nitride.

Further provided herein is a method of inactivating a pathogen by contacting a virus, bacteria, and/or fungus with an antipathogenic composition comprising silicon nitride. In an embodiment, the method may include coating a device or apparatus with silicon nitride and contacting the coated apparatus with the virus, bacterium, or fungus. Coating the apparatus may include applying a silicon nitride powder to a surface of the apparatus. In other embodiments, the silicon nitride powder may be incorporated within the device or apparatus.

In further embodiments, the method may include contacting a silicon nitride slurry with the surface of living agricultural plants, trees, grains, etc. infected with a plant-based pathogen. In an embodiment, infected leaves may be sprayed with an about 1 vol. % to about 40 vol % slurry of silicon nitride in water. The leaves may be exposed to the silicon nitride slurry for at least 1 minute, at least 5 minutes, at least 10 minutes, at least 20 minutes, at least 30 minutes, at least 1 hour, at least 2 hours, at least 5 hours, or at least 1 day. In various examples, the infected area of leaves may be reduced by at least 50%, at least 60%, at least 70%, at least 80%, at least 90%, at least 95%, or at least 99%. In an example, after 1 minute of exposure, the infected area of the leaves may be reduced by about 95%.

Without being limited to a particular theory, the antipathogenic composition may decrease viral action by alkaline transesterification and reduce the activity of hemagglutinin. It was surprisingly found that silicon nitride powder (i) remarkably decreases viral action by alkaline transesterification through the breakage of RNA internucleotide linkages and (ii) markedly reduced the activity of hemagglutinin thus disrupting host cell recognition by denaturing protein structures on viral surfaces leading to the inactivation of viruses regardless of the presence of a viral envelope.

In an embodiment, the antipathogenic composition may exhibit elution kinetics that show: (i) a slow but continuous elution of ammonia from the solid state rather than from the usual gas state; (ii) no damage or negative effect to cells; and (iii) an intelligent elution increasing with decreasing pH. Moreover, the inorganic nature of silicon nitride may be more beneficial than the use of petrochemical or organometallic fungicides which are known to have residual effects in soil, on plants, and in their fruit.

It was also surprisingly found that silicon nitride particles may be electrically attracted to and attach to the spores of the pathogen.

Also provided herein is a method of treating or preventing a pathogen at a location in a human patient. For example, the pathogen may be a virus, bacterium, or fungus. The method may include contacting the patient with a device, apparatus, or composition comprising silicon nitride. Without being limited to any one theory, the silicon nitride inactivates the virus (for example, Influenza A), bacterium, or fungus. The device, apparatus, or composition may include about 1 wt. % to about 100 wt. % silicon nitride. In some examples, the device or apparatus may include about 1 wt. % to about 100 wt. % silicon nitride on the surface of the device or apparatus. In an embodiment, the device or apparatus may be a monolithic silicon nitride ceramic. In another embodiment, the device or apparatus may include a silicon nitride coating, such as a silicon nitride powder coating. In another embodiment, the device or apparatus may incorporate silicon nitride into the body of the device. For example, silicon nitride powder may be ground in or otherwise incorporated into the body of the device or apparatus using methods known in the art.

In some embodiments, the device or apparatus may be contacted with the patient for at least 1 minute, at least 5 minutes, at least 30 minutes, at least 1 hour, at least 2 hours, at least 5 hours, or at least 1 day. In at least one example, the device or apparatus may be permanently implanted in the patient.

Also provided herein is a method of treating or preventing a pathogen at a location in a plant. For example, the pathogen may be a virus, bacterium, or fungus. The method may include contacting the plant with a composition comprising silicon nitride. Without being limited to any one theory, the silicon nitride inactivates the virus, bacterium, or fungus (for example, *Plasmopara viticola*). In some embodiments, the composition may include a silicon nitride slurry in water containing up to 40 vol. % silicon nitride with appropriate dispersants and slurry stabilization agents. The composition may be applied to living agricultural plants, trees, grains and the like to inactivate and kill or prevent the growth of viruses, bacteria, and fungi after being in contact with them for at least 1 minute, at least 5 minutes, at least 30 minutes, at least 1 hour, at least 2 hours, at least 5 hours, or at least 1 day.

EXAMPLES

Example 1: Effect of Silicon Nitride Concentration on Virus Inactivation

Figure 2A:
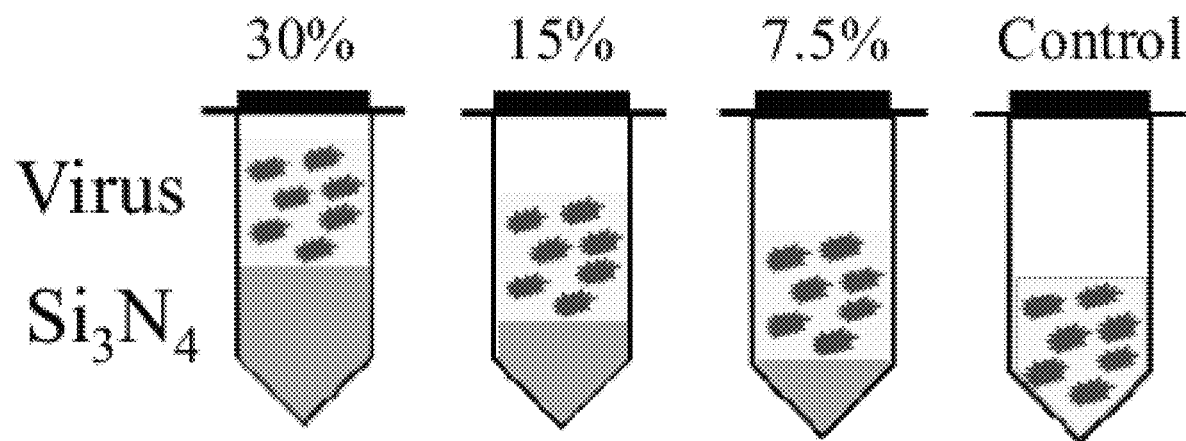
FIG. 2A is an illustration of a virus exposed to 0 wt. %, 7.5 wt. %, 15 wt. %, and 30 wt. % $Si_3N_4$ for 10 minutes.

To show the effect of silicon nitride concentration on the inactivation of viruses, Influenza A was exposed to various concentrations of $Si_3N_4$ powder. To prepare the silicon nitride, a specific weight of silicon nitride powder mixed with pure distilled water. For instance, 7.5 g of silicon nitride was dispersed in 92.5 g of pure distilled water. The virus was added to this mixture in concentrations of 1:1, 1:10 and 1:100 virus/mixture, respectively. These mixtures were then allowed to incubate under gentle agitation for 10 minutes at 4° C. Influenza A was exposed to 0 wt. %, 7.5 wt. %, 15 wt. %, and 30 wt. % $Si_3N_4$ for 10 minutes at 4° C., as illustrated in FIG. 2A. The mixtures were then filtered to remove the silicon nitride powder.

Figure 2B:
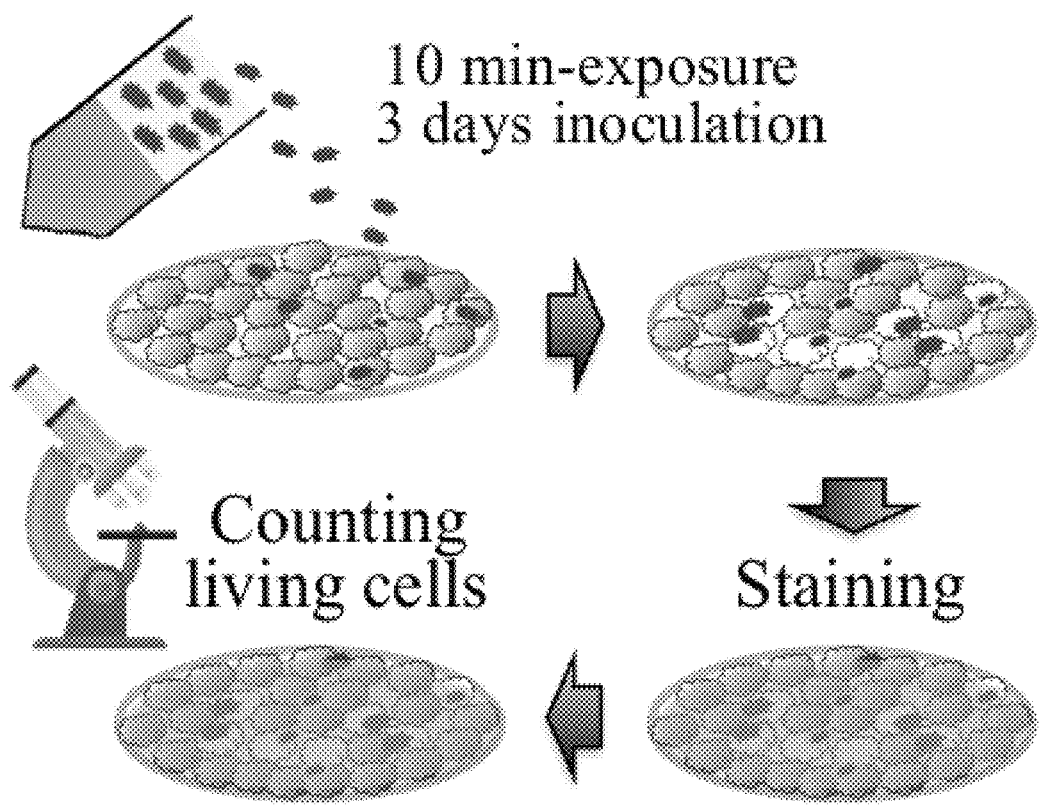
FIG. 2B is an illustration of methods used to determine viability of cells inoculated with a virus exposed to $Si_3N_4$ according to FIG. 2A.

Influenza A virus-inoculated Madin-Darby canine kidney (MDCK) cells were then observed for the effectiveness of $Si_3N_4$ in inactivating the Influenza A. The remaining mixtures were then inoculated into Petri dishes containing living MDCK cells within a biogenic medium. The amount of living MDCK cells were subsequently counted using staining methods after 3 days exposure. The viability of MDCK cells was determined after inoculating the cells for 3 days with Influenza A exposed to $Si_3N_4$ according to FIG. 2B.

Figure 4A:
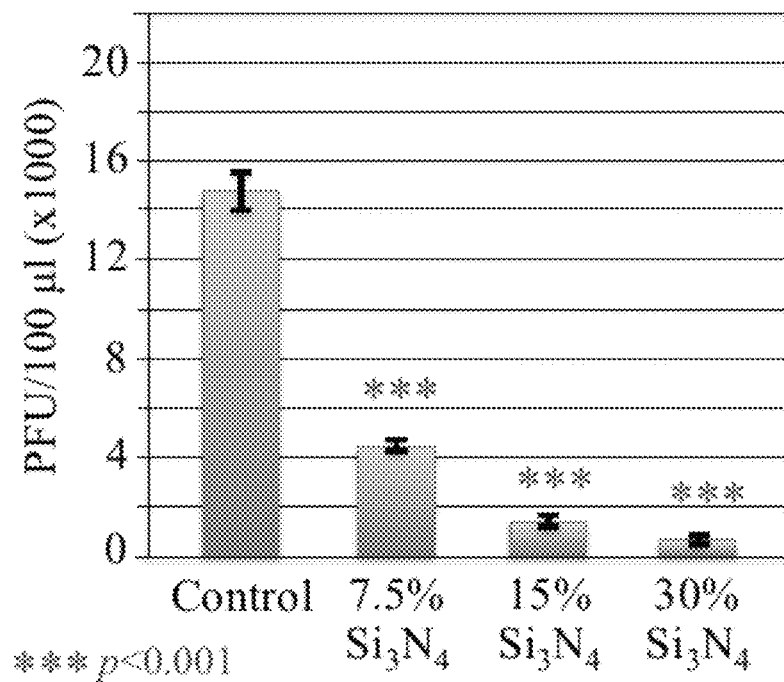
FIG. 4A is a graph of PFU/100 µl for Influenza A exposed to 0 wt. %, 7.5 wt. %, 15 wt. %, and 30 wt. % $Si_3N_4$ for 10 minutes according to FIG. 2A.
Figure 4B:
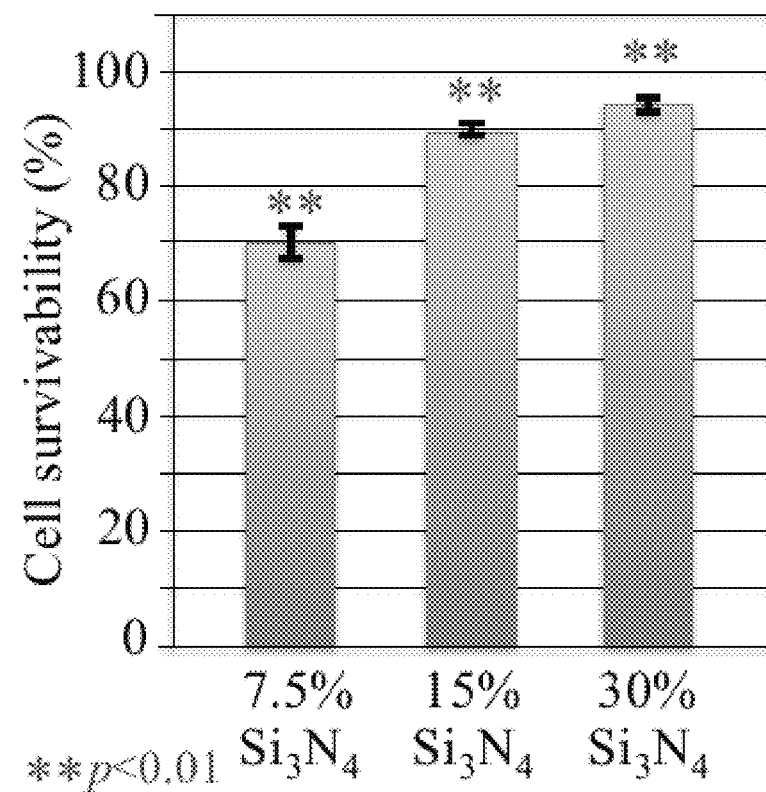
FIG. 4B is a graph of cell survivability of cells inoculated with Influenza A exposed to 7.5 wt. %, 15 wt. %, and 30 wt. % $Si_3N_4$ for 10 minutes according to FIG. 2B.
Figure 5:
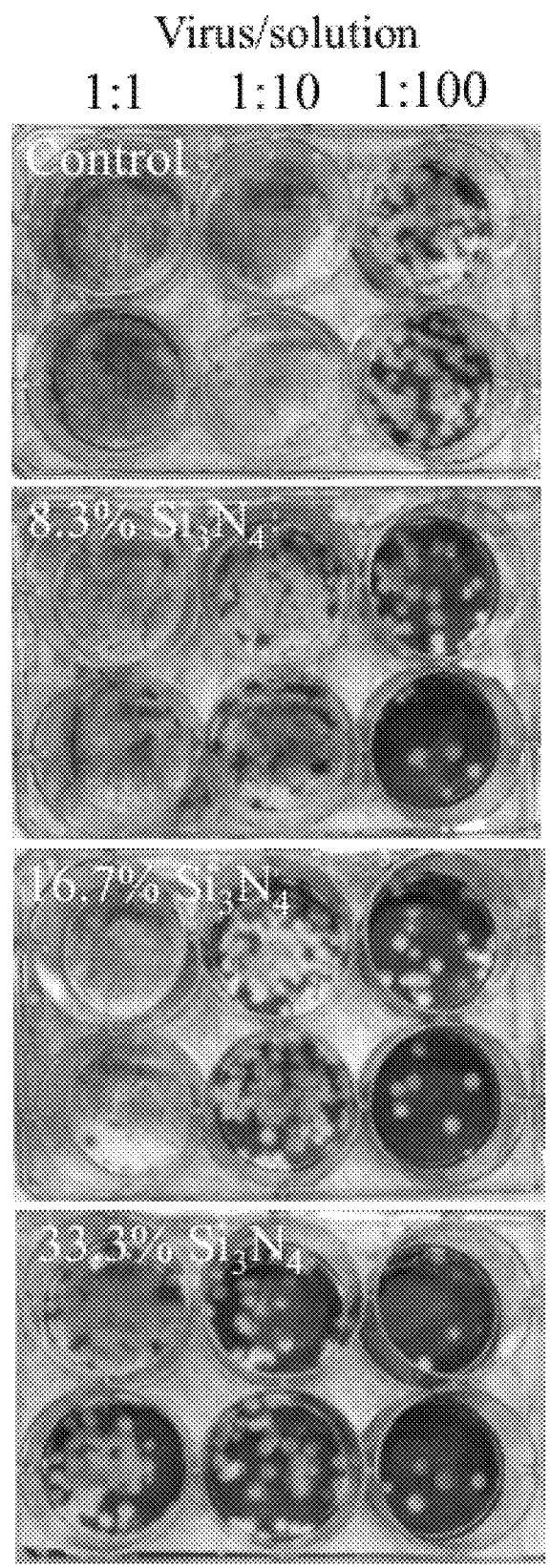
FIG. 5 includes photographs of cells inoculated with different ratios of virus to slurry that had been exposed to various concentrations of $Si_3N_4$.

FIG. 4A is a graph of PFU/100 µl for Influenza A exposed to 0 wt. %, 7.5 wt. %, 15 wt. %, and 30 wt. % $Si_3N_4$ for 10 minutes. FIG. 4B is a graph of cell survivability of cells inoculated with Influenza A exposed to 7.5 wt. %, 15 wt. %, and 30 wt. % $Si_3N_4$ for 10 minutes.

Example 2: Effect of Exposure Time and Temperature on Virus Inactivation

Figure 3A:
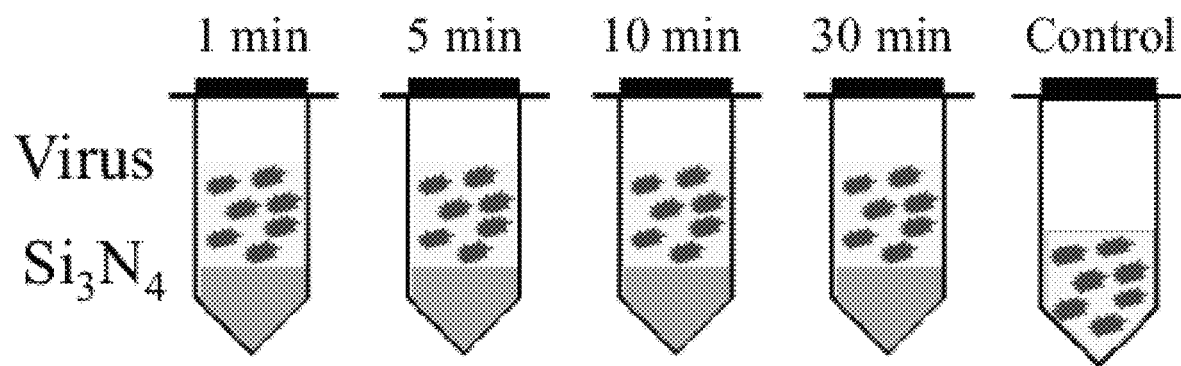
FIG. 3A is an illustration of a virus exposed to 15 wt. % $Si_3N_4$ for 1, 5, 10, and 30 minutes.
Figure 3B:
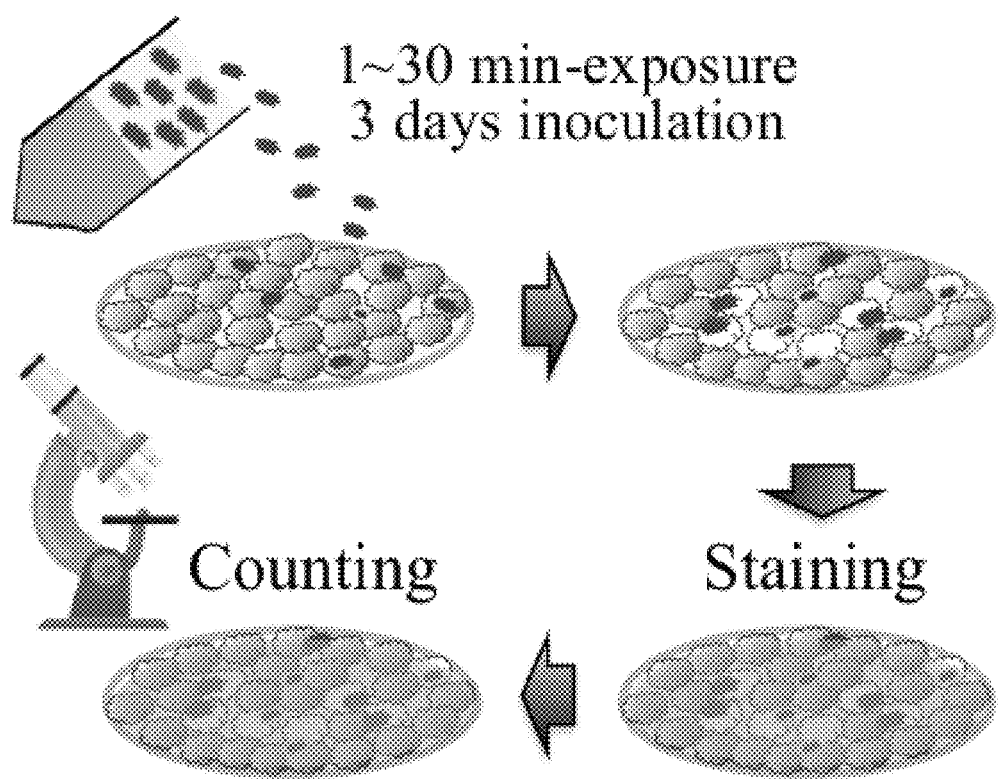
FIG. 3B is an illustration of methods used to determine viability of a virus after exposure to $Si_3N_4$ according to FIG. 3A.

To show the effect of silicon nitride on the inactivation of viruses, Influenza A was exposed to a fixed concentration of $Si_3N_4$ powder (15 wt. %) for various times and temperatures. The mixture was then allowed to incubate under gentle agitation for 1-30 minutes at room temperature and at 4° C. For example, Influenza A was exposed to 15 wt. % $Si_3N_4$ for 1, 5, 10, or 30 minutes at room temperature or 4° C., as illustrated in FIG. 3A. Influenza A virus-inoculated Madin-Darby canine kidney (MDCK) cells were then observed for the effectiveness of $Si_3N_4$ in inactivating the Influenza A. The viability of MDCK cells was determined after inoculating the cells for 3 days with Influenza A exposed to $Si_3N_4$ according to FIG. 3B.

Figure 7A:
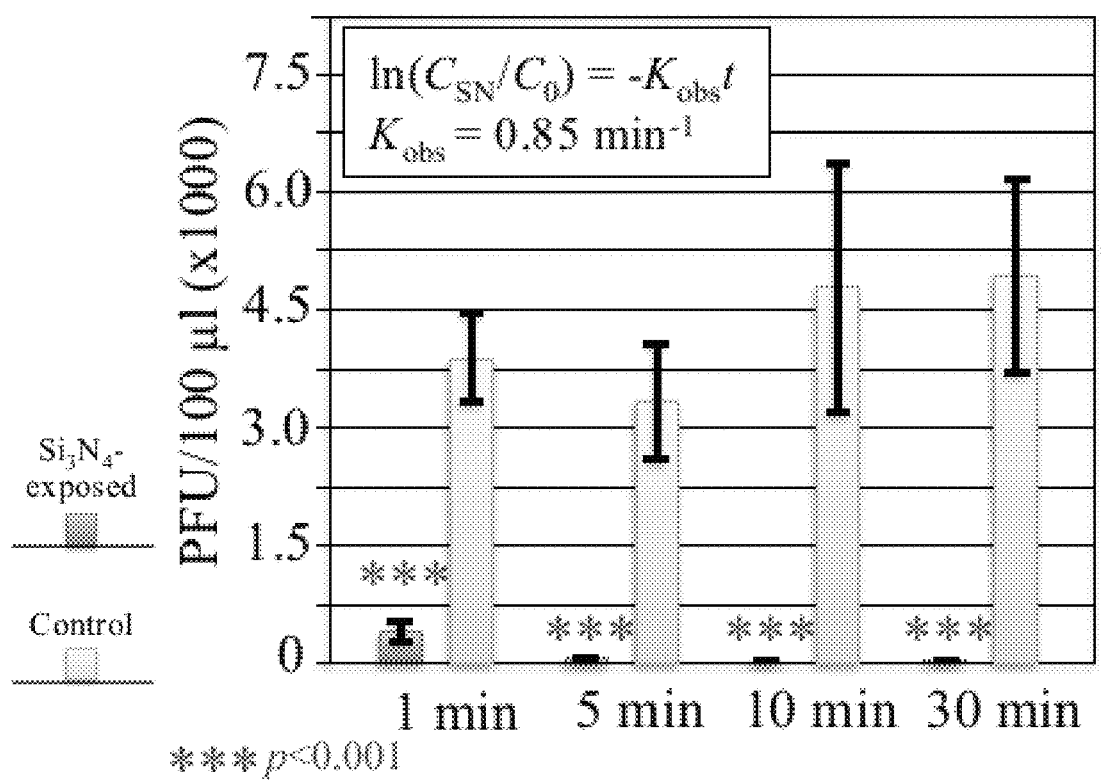
FIG. 7A is a graph of PFU/100 µl for Influenza A exposed to 15 wt. % $Si_3N_4$ for 1 minute, 5 minutes, 10 minutes, or 30 minutes at room temperature.
Figure 7B:
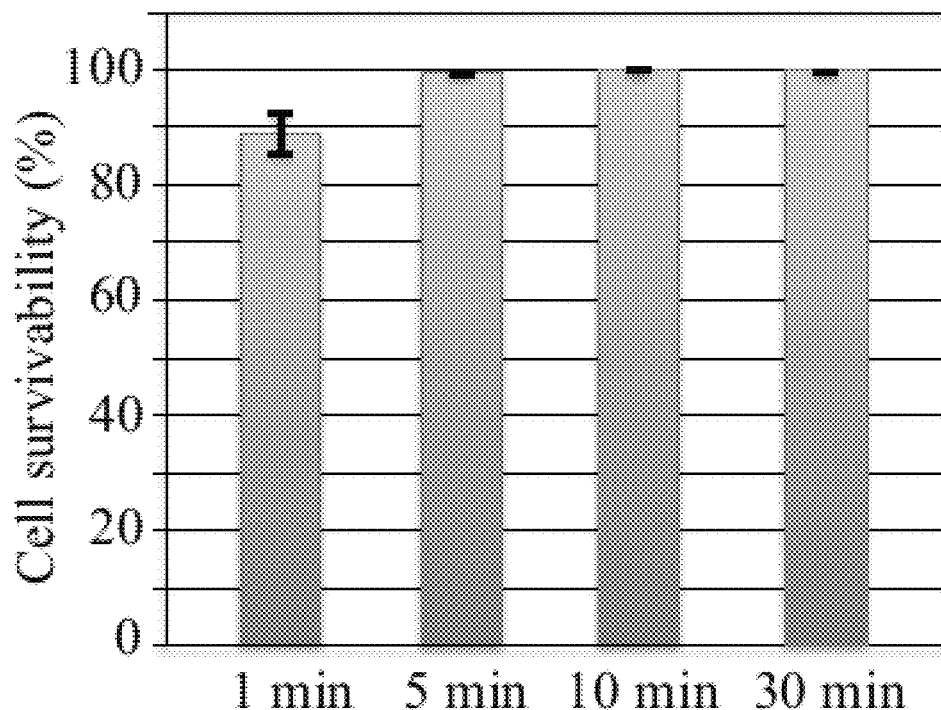
FIG. 7B is a graph of cell survivability of cells inoculated with Influenza A exposed to 15 wt. % $Si_3N_4$ for 1 minute, 5 minutes, 10 minutes, or 30 minutes at room temperature.

FIG. 7A is a graph of PFU/100 µl for Influenza A exposed to 15 wt. % $Si_3N_4$ for 1 minute, 5 minutes, 10 minutes, or 30 minutes at room temperature. FIG. 7B is a graph of cell survivability of cells inoculated with Influenza A exposed to 15 wt. % $Si_3N_4$ for 1 minute, 5 minutes, 10 minutes, or 30 minutes at room temperature.

Figure 8A:
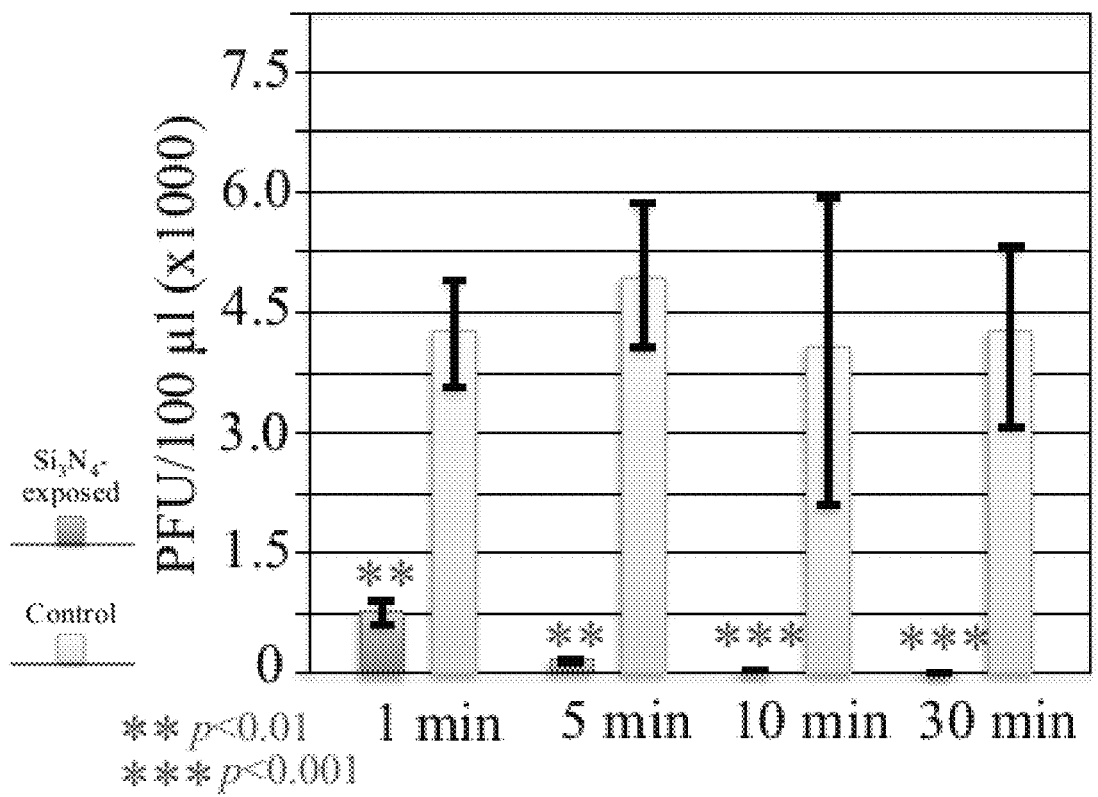
FIG. 8A is a graph of PFU/100 µl for Influenza A exposed to 15 wt. % $Si_3N_4$ for 1 minute, 5 minutes, 10 minutes, or 30 minutes at 4° C.
Figure 8B:
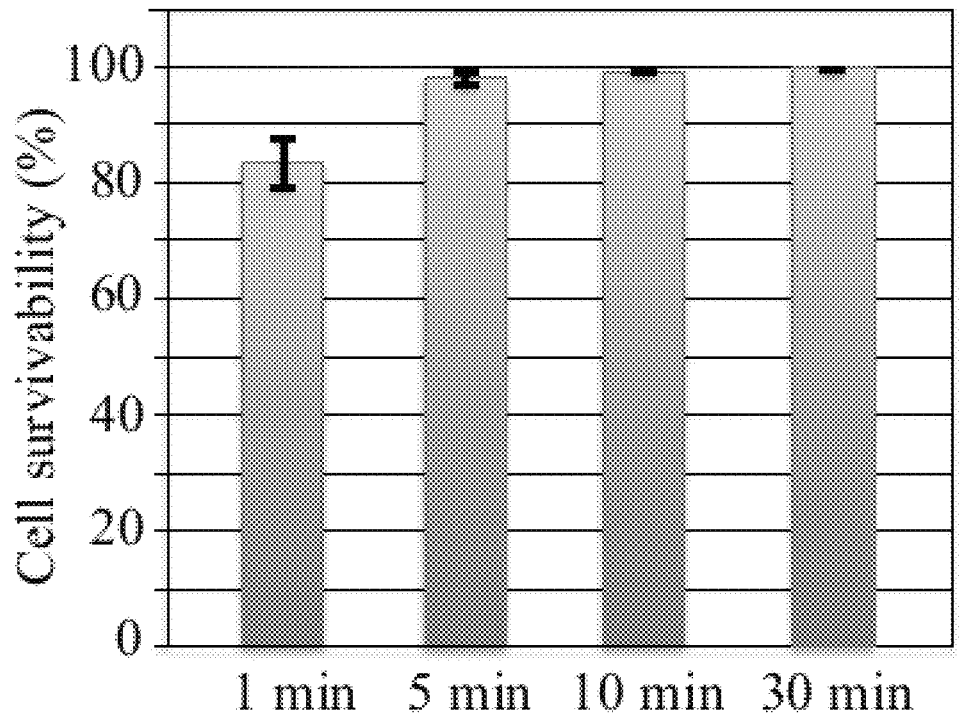
FIG. 8B is a graph of cell survivability of cells inoculated with Influenza A exposed to 15 wt. % $Si_3N_4$ for 1 minute, 5 minutes, 10 minutes, or 30 minutes at 4° C.
Figures 9A, 9B:
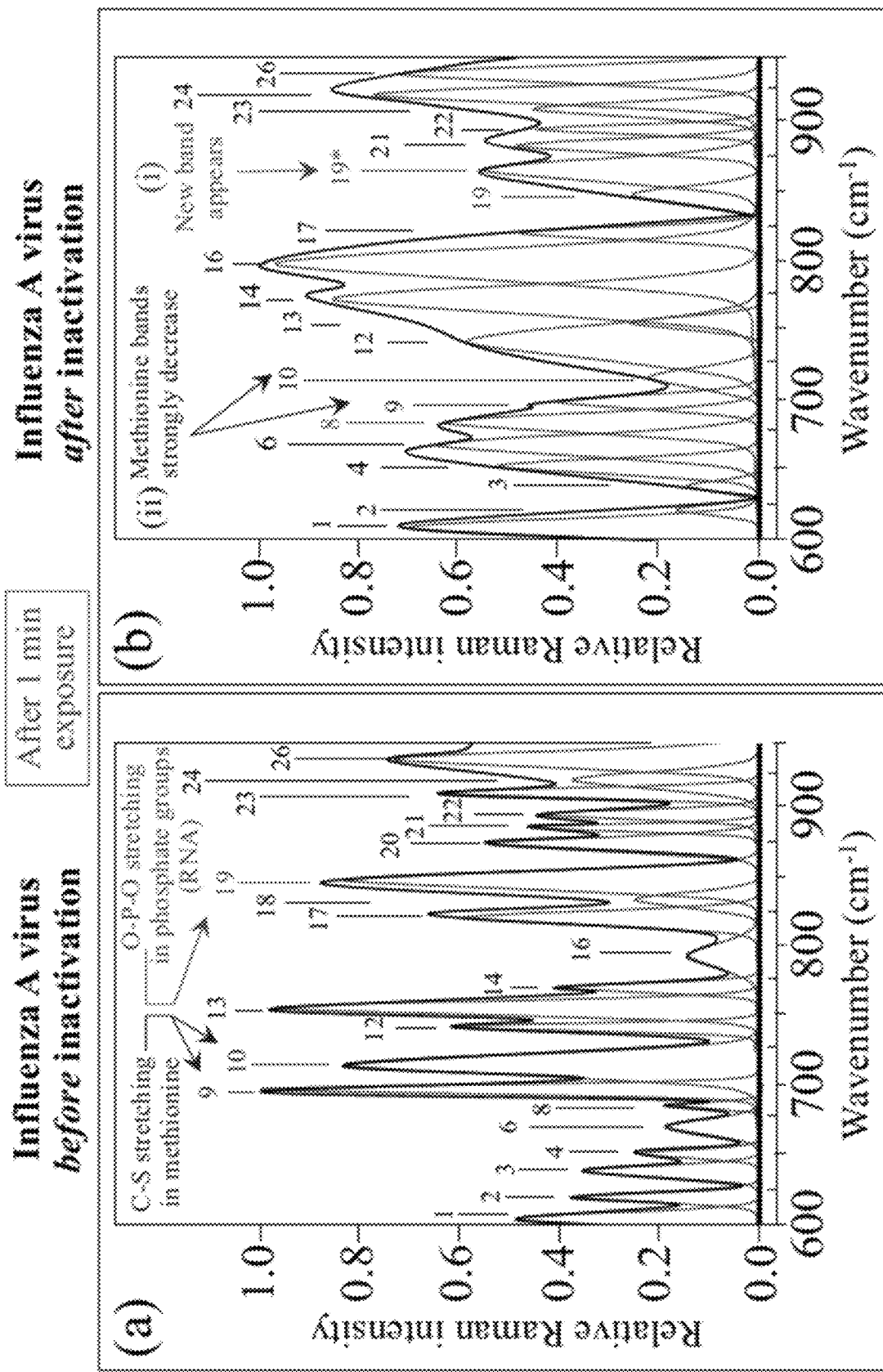
FIG. 9A shows the Raman spectrum of Influenza A virus before inactivation.
FIG. 9B shows changes in the Raman spectrum of the Influenza A virus relevant to chemical modifications in RNA and hemagglutinin after inactivation after 1 minute of exposure.
Figure 11:
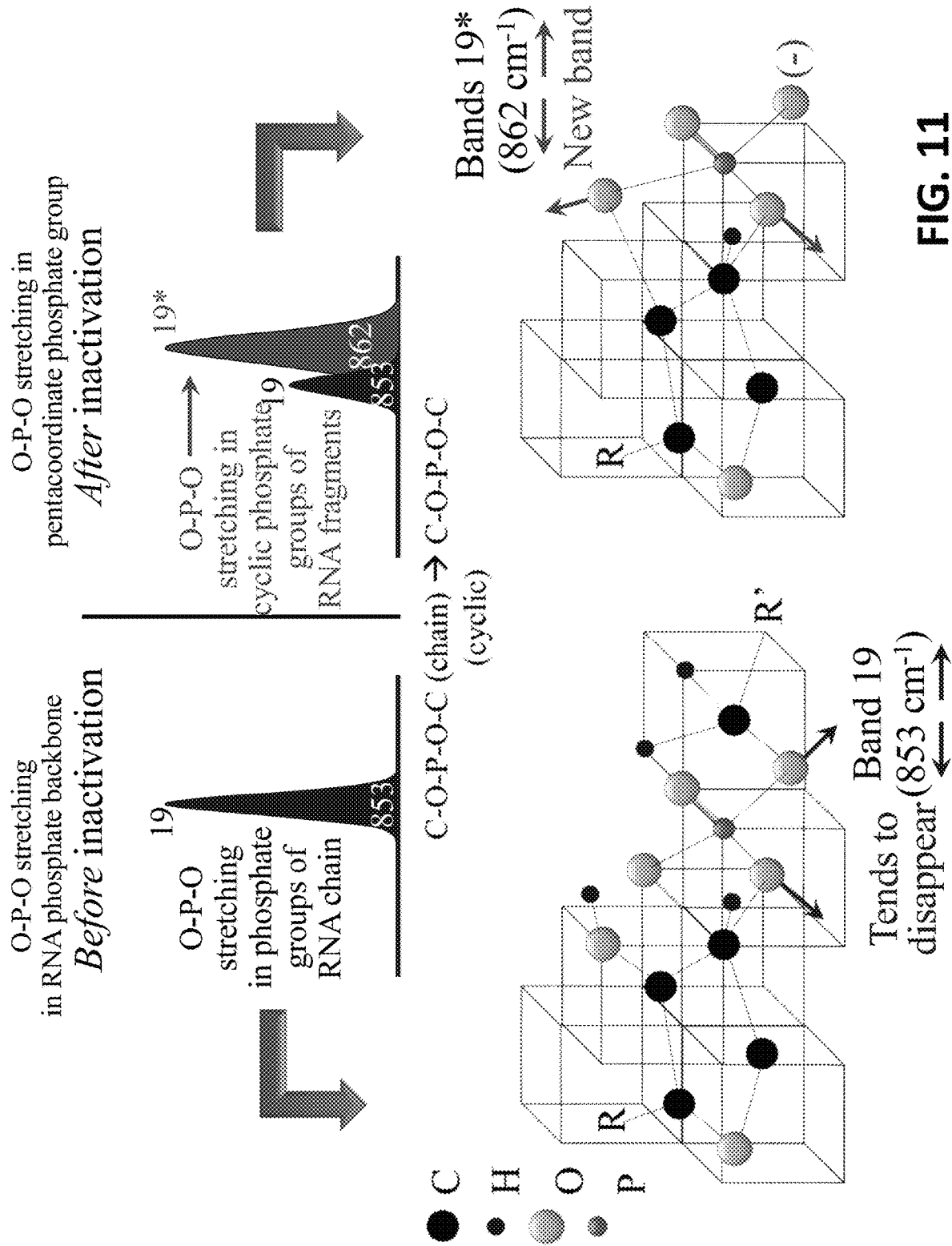
FIG. 11 shows O—P—O stretching in pentacoordinate phosphate group after inactivation.
Figure 12B:
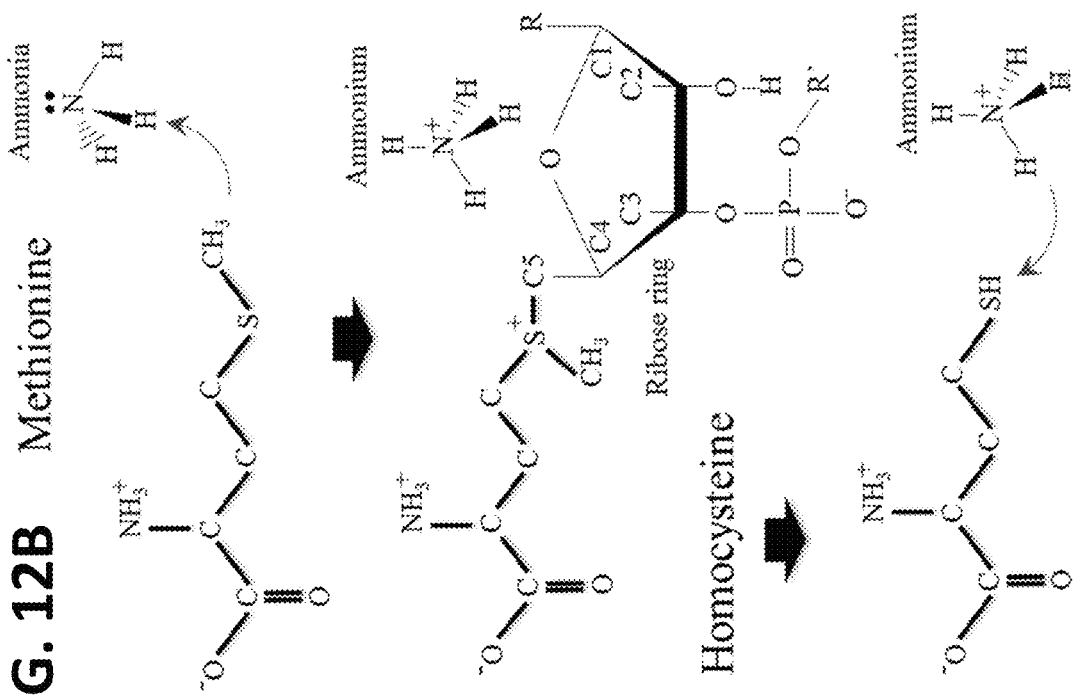
FIG. 12B shows methionine's structural change in the presence of ammonia.
Figure 12A:
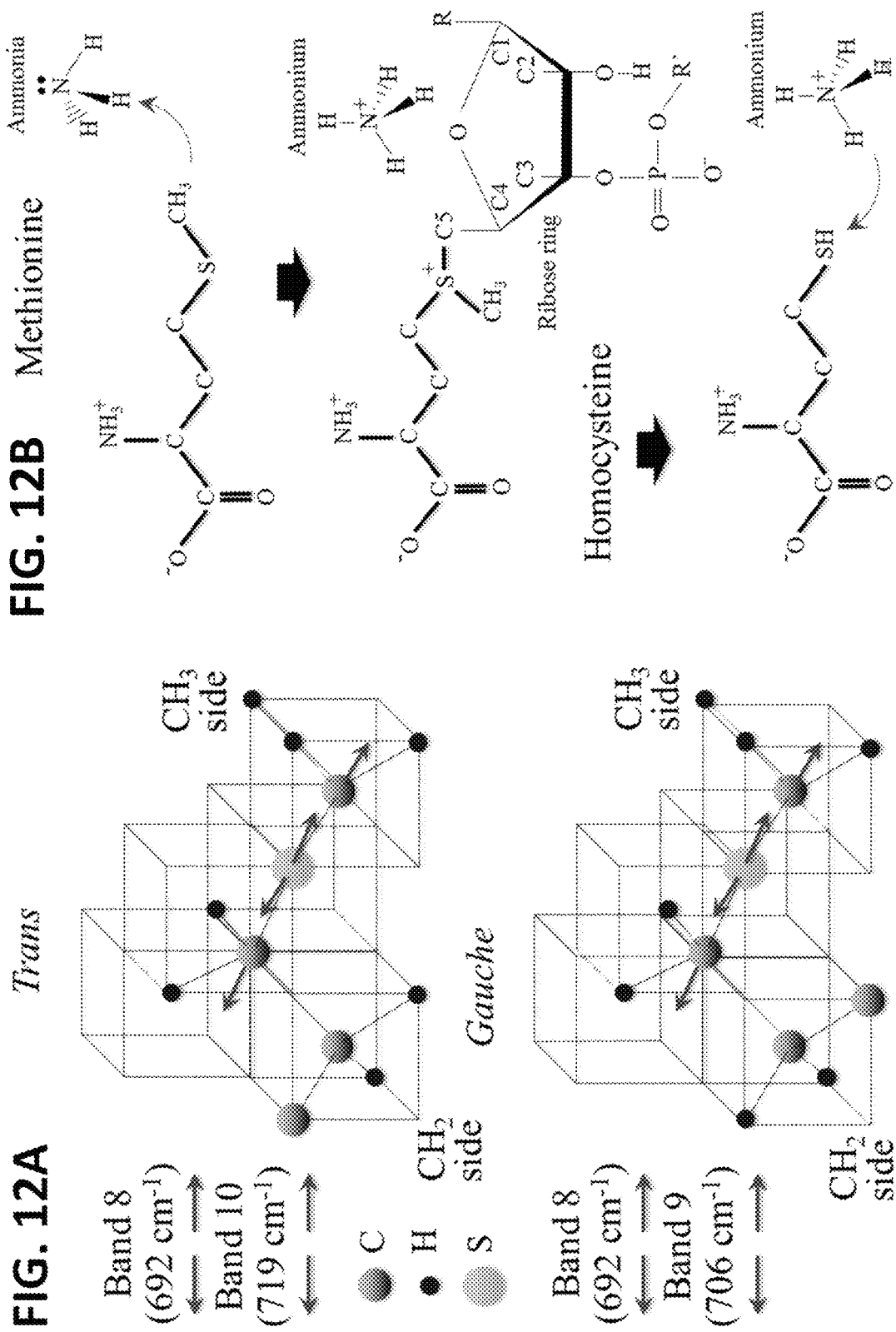
FIG. 12A shows vibrational modes of methionine in the hemagglutinin structure.
Figure 13:
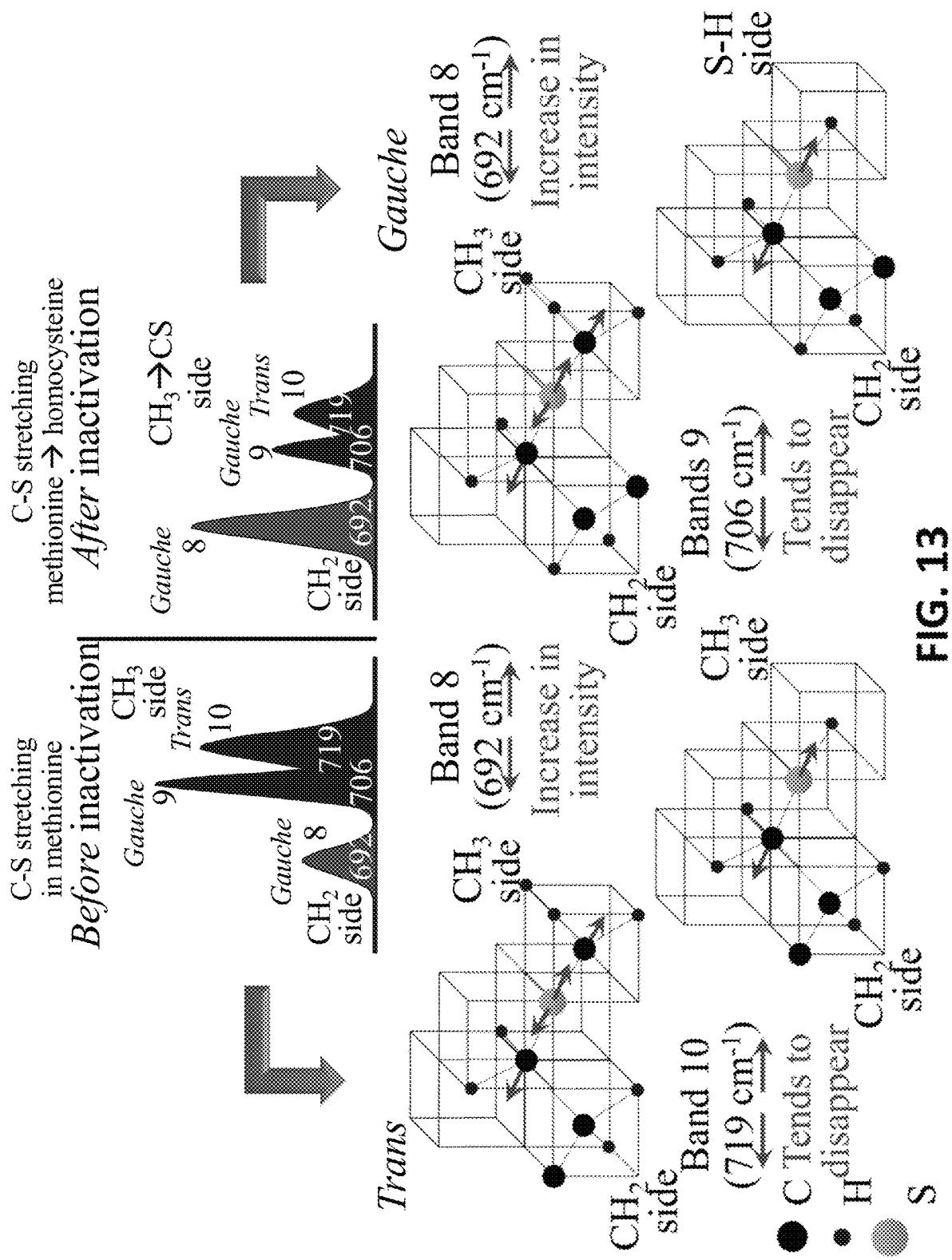
FIG. 13 shows C—S stretching methionine to homocysteine after inactivation.
Figure 14A:
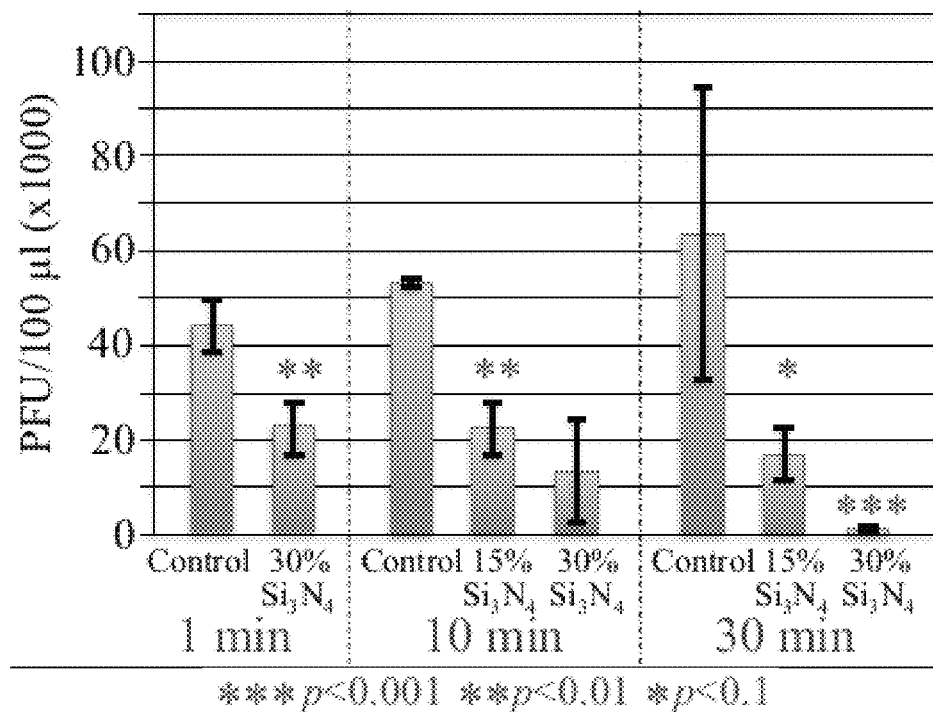
FIG. 14A is a graph of PFU/100 µl for Feline calicivirus exposed to 15 wt. % or 30 wt. % $Si_3N_4$ for 1 minute, 10 minutes, or 30 minutes.
Figure 14B:
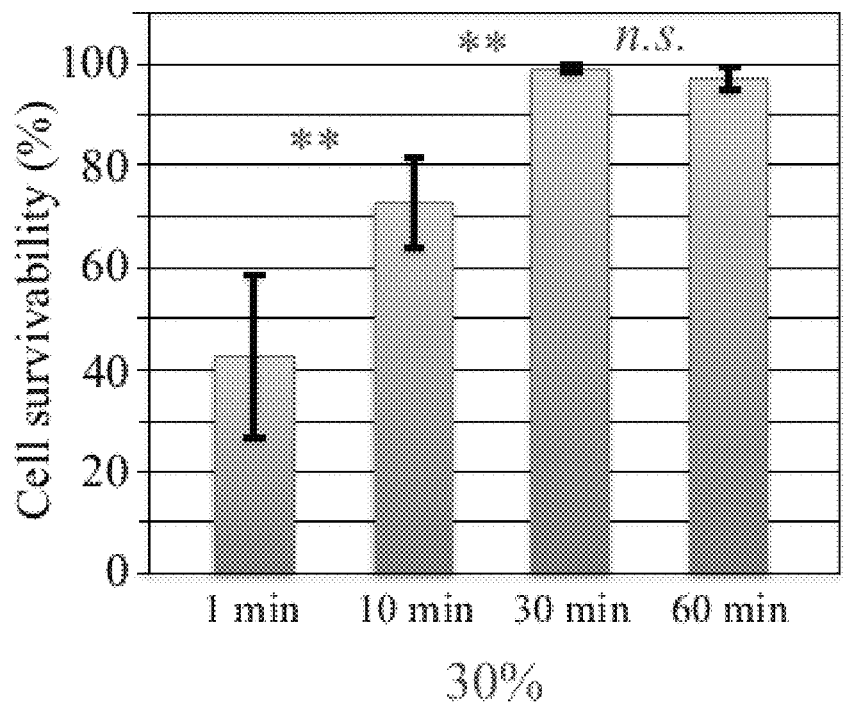
FIG. 14B is a graph of cell survivability of cells inoculated with Feline calicivirus exposed to 30 wt. % $Si_3N_4$ for 1 minute, 10 minutes, 30 minutes, or 60 minutes.

FIG. 8A is a graph of PFU/100 µl for Influenza A exposed to 15 wt. % $Si_3N_4$ for 1 minute, 5 minutes, 10 minutes, or 30 minutes at 4° C. FIG. 8B is a graph of cell survivability of cells inoculated with Influenza A exposed to 15 wt. % $Si_3N_4$ for 1 minute, 5 minutes, 10 minutes, or 30 minutes at 4° C.

Example 3: Effect of Silicon Nitride on H1H1 Influenza a Inactivation

To show the effect of silicon nitride on the inactivation of viruses, Influenza A was exposed to a slurry of 15 wt. % silicon nitride for 10 minutes.

Figure 15A:
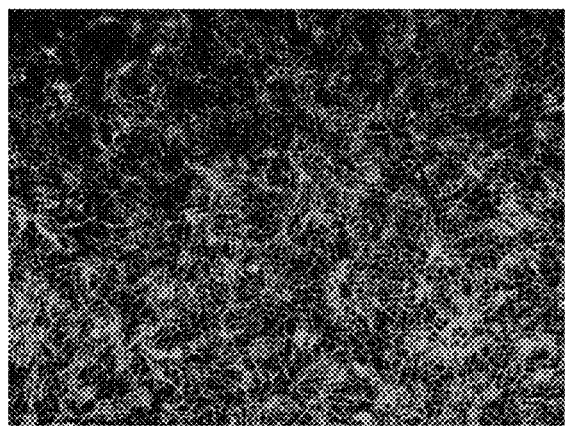
FIG. 15A shows the H1 H1 Influenza A virus (nucleoprotein, NP) stained red after 10 minutes of exposure to a slurry of 15 wt. % silicon nitride and after its inoculation into a biogenic medium containing MDCK cells stained green for the presence of filamentous actin (F-actin) proteins.
Figure 15B:
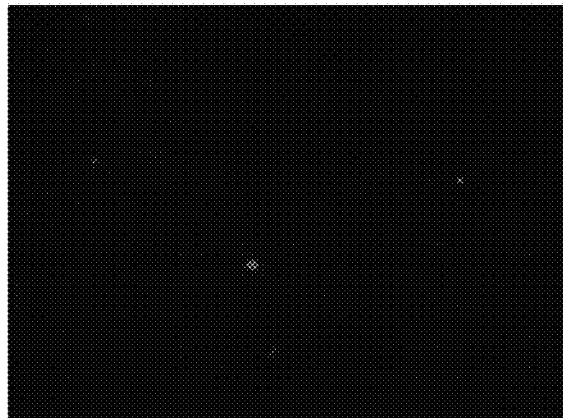
FIG. 15B shows the NP stained H1H1 Influenza A virus from FIG. 15A.
Figure 15C:
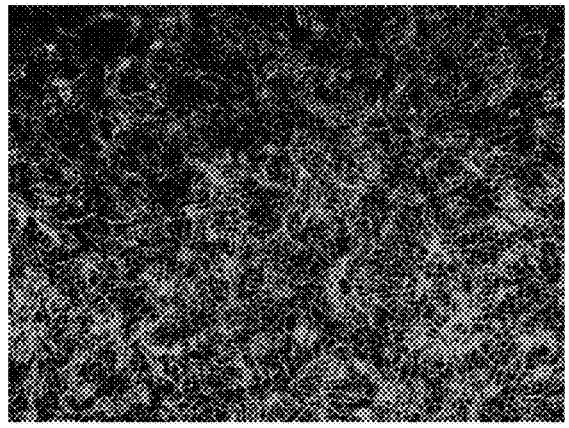
FIG. 15C shows the F-actin stained MDCK cells from FIG. 15A.
Figure 16A:
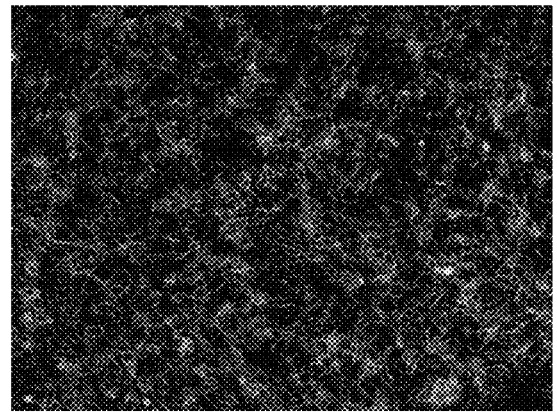
FIG. 16A shows the H1 H1 Influenza A virus (nucleoprotein, NP) stained red without exposure to silicon nitride and after its inoculation into a biogenic medium containing MDCK cells stained green for the presence of filamentous actin (F-actin) proteins.
Figure 16B:
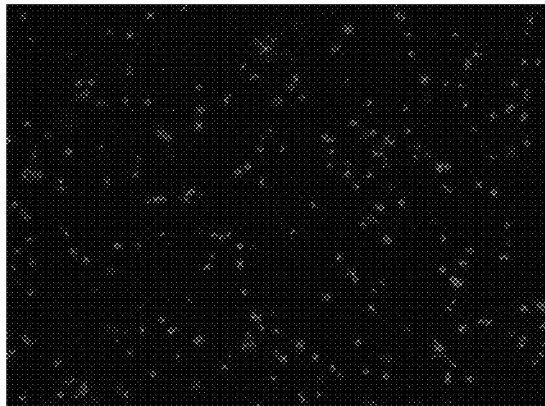
FIG. 16B shows the NP stained H1H1 Influenza A virus from FIG. 16A.
Figure 16C:
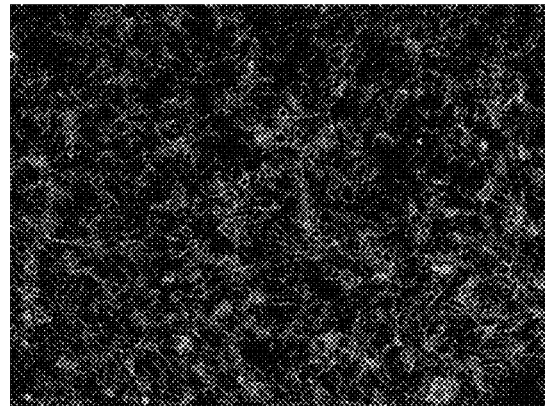
FIG. 16C shows the F-actin stained MDCK cells from FIG. 16A.

FIGS. 15A-15C show the H1H1 Influenza A virus (A/Puerto Rico/8/1934 H1N1 (PR8)) stained red (nucleoprotein, NP) after its inoculation into a biogenic medium containing MDCK cells stained green for the presence of filamentous actin (F-actin) proteins which are found in all eukaryotic cells. FIGS. 16A-16C shows the effect of the virus on the MDCK cells without the presence of silicon nitride.

Example 4: Effect of Silicon Nitride on *Plasmopara Viticola*

To show the effect of silicon nitride on the inactivation of agricultural fungi, Cabernet Sauvignon leaves were infected with *Plasmopara viticola* at a concentration of $3 \times 10^4$ spore sacs/ml. Treated *Plasmopara viticola* was exposed to a slurry of 1.5 vol. % silicon nitride for 1 minute.

Figures 17A, 17B:
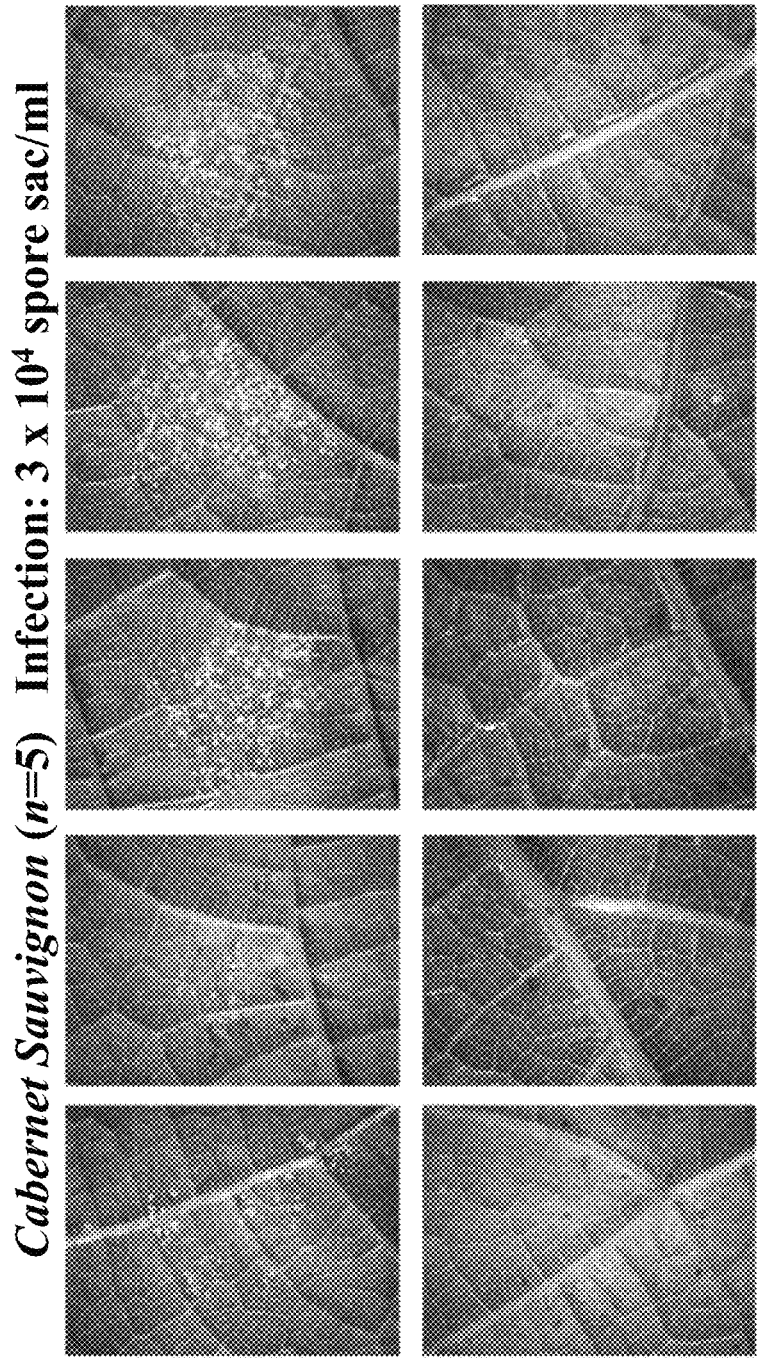
FIG. 17A shows Cabernet Sauvignon leaves inoculated with *Plasmopara viticola* untreated.
FIG. 17B shows Cabernet Sauvignon leaves inoculated with *Plasmopara viticola* treated for 1 minute with 1.5 vol. % $Si_3N_4$ powder.
Figure 19:
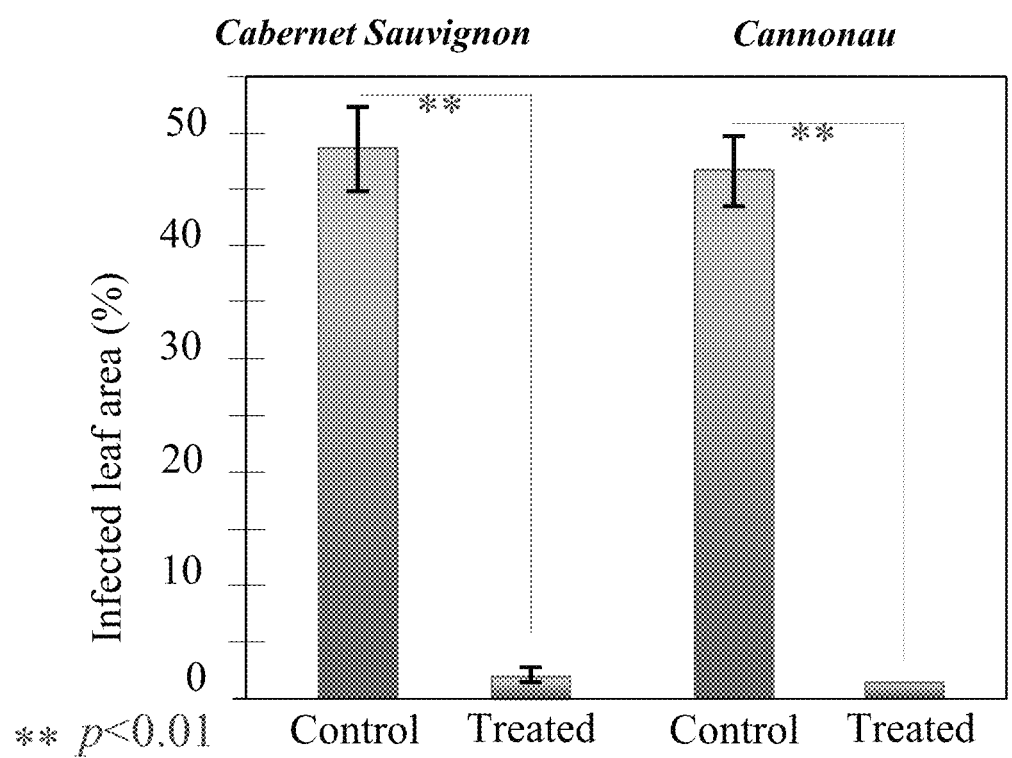
FIG. 19 is a graph of the infected leaf area of Cabernet Sauvignon and Cannonau leaves with control and treated *Plasmopara viticola*.

FIG. 17A shows untreated *Plasmopara viticola* fungi on Cabernet Sauvignon leaves. FIG. 17B shows treated *Plasmopara viticola* fungi on Cabernet Sauvignon leaves. It can be seen that the leaves inoculated with *Plasmopara viticola* treated for 1 minute with 1.5 vol. % $Si_3N_4$ powder have less of the fungi on the surface of the leaves. This is further evidenced by FIG. 19 which depicts the percentage of infected leaf area for both Cabernet Sauvignon and Cannonau leaves inoculated with control and treated *Plasmopara viticola*. FIG. 19 clearly shows a statistical significance win the infected leaf area between the control and treated fungi.

Figure 18A:
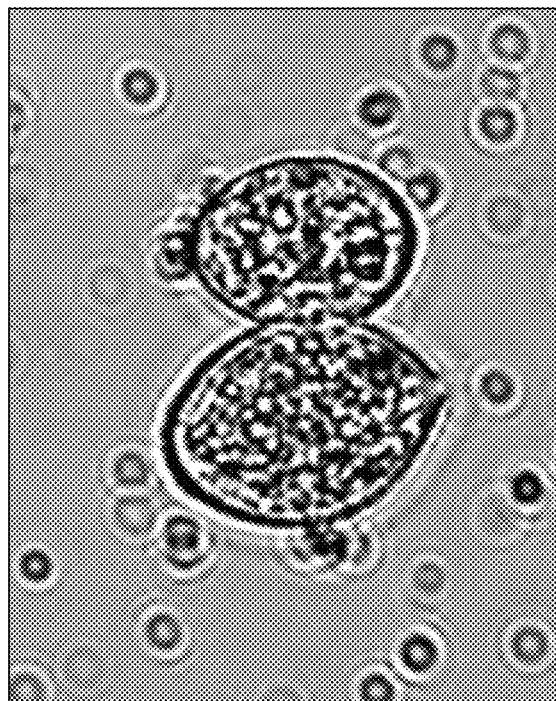
FIG. 18A shows untreated spore sacs.
Figure 18B:
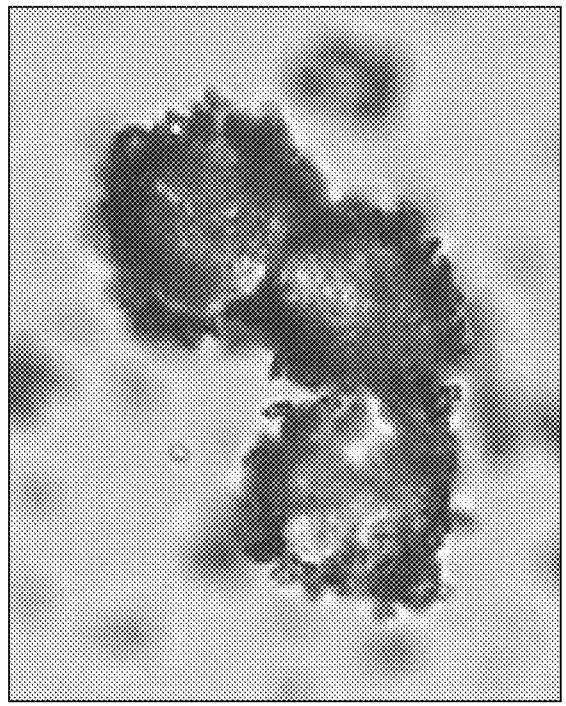
FIG. 18B shows spore sacs in the presence of $Si_3N_4$.

The silicon nitride particles appear electrically attracted to and attach themselves to the spores of the pathogen, as seen in FIG. 18B. FIG. 18A shows a microscopic image of untreated spore sacs of *Plasmopara viticola*, while FIG. 18B shows a microscopic image of spore sacs of *Plasmopara viticola* in the presence of $Si_3N_4$.

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A plant treatment composition effective in inactivating a plant pathogen on a plant comprising a slurry of water and silicon nitride, wherein the concentration of silicon nitride is about 1 vol. % to about 30 vol. %, and wherein the silicon nitride reduces the pathogen on the plant.

2. The composition of claim 1, wherein the concentration of silicon nitride is about 1.5 vol. %.

3. The composition of claim 1, wherein the concentration of silicon nitride is about 5 vol. % to about 30 vol. %.

4. The composition of claim 1, wherein the pathogen comprises a fungi.

5. The composition of claim 1, wherein the pathogen comprises *Plasmopara viticola*.

6. The composition of claim 4, wherein the plant comprises Cabernet Sauvignon or Cannonau.

7. The composition of claim 1, wherein the composition is effective in treating or preventing the pathogen on the plant.

8. A plant treatment composition effective in inactivating a plant pathogen on a plant comprising silicon nitride at a concentration of about 1 vol. % to about 5 vol. % and wherein the silicon nitride inactivates the pathogen on the plant.

9. The composition of claim 8, wherein the concentration of silicon nitride is about 1.5 vol. %.

10. The composition of claim 8, wherein the composition comprises a slurry of silicon nitride particles and water.

11. The composition of claim 8, wherein the pathogen comprises a fungi.

12. The composition of claim 8, wherein the pathogen comprises *Plasmopara viticola*.

13. The composition of claim 12, wherein the plant comprises Cabernet Sauvignon or Cannonau.

\* \* \* \* \*